(12) United States Patent
Chen et al.

(10) Patent No.: US 9,189,596 B2
(45) Date of Patent: Nov. 17, 2015

(54) MEASURING COGNITIVE LOAD

(75) Inventors: Fang Chen, Peakhurst (AU); Natalie Ruiz, Surry Hills (AU); Eric Choi, West Pennant Hills (AU)

(73) Assignee: NATIONAL ICT AUSTRALIA LIMITED, Eveleigh, NSW (AU)

( * ) Notice: Subject to any disclaimer, the term of this patent is extended or adjusted under 35 U.S.C. 154(b) by 1882 days.

(21) Appl. No.: 11/993,008

(22) PCT Filed: Jun. 28, 2006

(86) PCT No.: PCT/AU2006/000914
§ 371 (c)(1),
(2), (4) Date: Dec. 11, 2008

(87) PCT Pub. No.: WO2007/000030
PCT Pub. Date: Jan. 4, 2007

(65) Prior Publication Data
US 2010/0217097 A1    Aug. 26, 2010

(30) Foreign Application Priority Data

Jun. 29, 2005 (AU) ................................ 2005903441

(51) Int. Cl.
*A61B 5/00* (2006.01)
*G06F 19/00* (2011.01)
*A61B 5/16* (2006.01)

(52) U.S. Cl.
CPC . *G06F 19/34* (2013.01); *A61B 5/16* (2013.01); *A61B 5/4088* (2013.01); *A61B 5/7264* (2013.01); *A61B 5/7267* (2013.01)

(58) Field of Classification Search
CPC ...... A61B 5/4088; A61B 5/7264; A61B 5/16; A61B 5/7267; G06F 19/34
See application file for complete search history.

(56) References Cited

U.S. PATENT DOCUMENTS

| | | | |
|---|---|---|---|
| 5,447,166 A * | 9/1995 | Gevins | 600/544 |
| 5,687,291 A * | 11/1997 | Smyth | 706/10 |
| 5,689,619 A | 11/1997 | Smyth | |
| 6,061,610 A | 5/2000 | Boer | |
| 6,434,419 B1 * | 8/2002 | Gevins et al. | 600/544 |
| 6,842,877 B2 * | 1/2005 | Robarts et al. | 715/708 |
| 6,998,972 B2 * | 2/2006 | Geisler et al. | 340/439 |

(Continued)

FOREIGN PATENT DOCUMENTS

WO      WO 02/33529      4/2002

OTHER PUBLICATIONS

John Sweller et al., "Cognitive Architecture and Instructional Design", vol. 10, No. 3, 1998, pp. 251-296.

*Primary Examiner* — William Thomson
*Assistant Examiner* — Shirley Jian

(57) ABSTRACT

This invention concerns a method for measuring cognitive load of a person in performing a task. In other aspects the invention can be expressed as a computer and as software that are used to perform the method. The computer (50) has an interface having a plural number of unimodal input (20, 30 to 40) and output devices, and a cognitive load analyzer (50). The analyzer comprises a receiver to receive input data signal streams (25, 35 and 45) from respective devices (20, 30 and 40). A classifier (56 to 59), (66 to 69) and (76 to 79) is also provided to identify predetermined "meta-interaction patterns" from the streams (25, 35 and 45), and to weight the identified predetermined "meta-interaction patterns" to produce respective weighted outputs. A combiner (80) to fuse the outputs to produce a measure indicating the person's cognitive load.

24 Claims, 2 Drawing Sheets

(56) References Cited

U.S. PATENT DOCUMENTS

| | | | |
|---|---|---|---|
| 7,292,152 B2* | 11/2007 | Torkkola et al. | 340/439 |
| 7,565,230 B2* | 7/2009 | Gardner et al. | 701/32.7 |
| 8,020,104 B2* | 9/2011 | Robarts et al. | 715/744 |
| 2002/0091473 A1* | 7/2002 | Gardner et al. | 701/35 |
| 2004/0037236 A1 | 2/2004 | Massey et al. | |
| 2004/0088205 A1* | 5/2004 | Geisler et al. | 705/7 |
| 2004/0222892 A1 | 11/2004 | Balaban et al. | |
| 2004/0252027 A1* | 12/2004 | Torkkola et al. | 340/576 |

\* cited by examiner

MEASURING COGNITIVE LOAD

TECHNICAL FIELD

This invention concerns a method for measuring cognitive load. In other aspects the invention can be expressed as a computer and as software that are used to perform the method.

The concept of cognitive load has been used in a variety of fields that deal with the human mind interacting with some external stimulants. The definition of cognitive load is slightly different in each field. For instance, in pedagogical literature cognitive load refers to the total amount of mental activity imposed on working memory at any instance in time; while in ergonomics literature it is described as the portion of operator information processing capacity, or resources that are required to meet cognitive task demands. Each field provides different methods to measure cognitive load.

In this specification the phrase "cognitive load" is defined as in the cognitive psychology literature, and its meaning is not a measurement of attention span, stress, engagement or other external elements to a task. Cognitive load can be defined as the mental effort required for a particular person to comprehend or learn some material, or complete some task. Cognitive load is relative to both the user and the task being completed, at any single point in time.

BACKGROUND ART

Conventional methods for measuring cognitive load, include:
- subjective measures, such as self-rating scales;
- physiological techniques, such as pupil dilatation and heart rate;
- task or performance based measures, such as critical error rates; and
- behavioral measures, such as speech disfluencies, self-talk etc.

The are a number of problems with these methods for measuring cognitive load, including:
- some of the methods are intrusive and disrupt the normal flow of interaction;
- some of the methods are physically uncomfortable for the user;
- when conducted in real-time, some of the methods are labour-intensive;
- the data quality is potentially unreliable outside laboratory conditions; and
- the data quality can be affected by outside factors, such as user's stress level.

At this time there is no way to objectively quantify cognitive load that can be applied uniformly across fields as a standard, or to allow comparison between subjects. In fact, historically, the most consistent results for cognitive load assessments have been achieved through self-rating subjective measures; these allow users to describe in fine detail, their perceived level of cognitive load induced by various types of task.

A multimodal interface is an interface where the user is able to select one or more unimodal input or output devices to operate the interface. Use of each device represents a single mode of input or output. Most interfaces offer at least two input modes, keyboard and mouse. Multimodal interfaces typically offer more options, including for instance voice recognition and other less common modalities.

DISCLOSURE OF THE INVENTION

In a multimodal interaction scenario, a user experiencing a high cognitive load will show involuntary behavioral anomalies that the inventors have come to understand to be symptoms (both physical and otherwise) of cognitive overload. These symptoms may be caused by high load or actual symptoms that are displayed when dealing with a high load. Additionally, the user may also change the manner in which they operate the multimodal interface to communicate. For instance, users may:
- Continually move their mouse over a series of choices for an inordinately long time;
- Start shaking involuntarily;
- Make more non-critical mistakes in their interaction;
- Change their mind more frequently than usual; or,
- Use particular kinds of multimodal constructions more often; or
- Rely more on their more dominant modality than others.

Many other behavioral changes are also observable, but all the changes of interest concern the user's multimodal production or communicative act, rather than the content of the communication. The inventors refer to these as "meta-interaction features". A "meta-interaction pattern" is a predetermined combination of "meta-interaction features."

Recording these behavioral anomalies is akin to capturing prosodic information, or disfluencies from a speech signal—but extended to multimodal interaction input channels. While they are an inherent part of the interaction, these anomalies are rarely deliberate or conscious reactions.

In consequence the inventors propose a method for measuring a person's cognitive load, comprising the steps of:
- Receiving one or more input data streams from an interface being used by a person while performing a task;
- Identifying predetermined "meta-interaction patterns" from the streams;
- Weighting the identified predetermined "meta-interaction patterns" to produce respective outputs; and
- Fusing the outputs to produce a measure indicating the person's cognitive load.

The interface may be a multimodal interface.

The method may be unobtrusively performed to provide a real-time assessment of a user's cognitive load without attaching any devices to a user's body. Furthermore the measure may be objective.

The received input data streams may involve one or more of the following types of information:
- Visual, including eye movements, facial expressions, and gestures, such as deistic hand gestures, hand shapes, gesture trajectories, circling, underlining and various getural marking methods. Visual data stream may be infrared red images of the head, body or hand.
- Speech, including pitch and fundamental frequency and its associated higher order statistics, sound emissions (such as self-talk, mumbling and other verbal sounds), speech rate, and information throughput.
- Interaction events such as mouse hovering, mouse trajectory, menu and button selections, and typing and input method speed.
- Task characteristics such as task complexity or difficulty, current stage or state of the task, error rate, completion rate, and latency to respond.
- User characteristics such as gender, age and education.
- Physiological data such as heart rate and perspiration.

The method may further comprise the step of selecting input data streams, "meta-interaction patterns", method of performing the step of weighting and/or method of performing the step of fusing that are specific to the person. Further, the method may further comprise the step of selecting input data streams, "meta-interaction patterns", method of performing the step of weighting and/or method of performing the step of fusing that are specific to the task. For example, different classifiers will be derived for each type of input stream, and not all patterns may be present in every user. Therefore the classifiers will change for any user/task instance.

The step of identifying predetermined "meta-interaction patterns" from the streams may involve the steps of identifying predetermined features in each stream and then identifying patterns among the features. The features that are chosen depend on the available input streams and whether the system deems there to be a significant pattern found in that input stream, for that user. The type and number of input streams is therefore flexible.

The features are then recognised and fused together to acquire a reliable measure of the cognitive load. The fusion method will also depend on the available feature weights and may have several levels of incremental fusion, where small sets of features that are available are combined together first, before being combined with all available features.

The patterns may be identified using one of more of the following models:
Gaussian mixture models.
Hidden Markov models.
Linear discriminant analysis.
Decision trees.
Artificial neural networks.
Other statistical or non-statistical models.

The fusion step may be based on a probabilistic framework. Specifically it might be computing the probability of a set of features (X) indicating certain cognitive load level ($\theta$) and is given by:

$$P(\theta \mid X) = \sum_{m=1}^{M} P(C_m \mid X) \sum_{\tilde{\theta}} P(\tilde{\theta} \mid X, C_m) P(\theta \mid \tilde{\theta}, X, C_m)$$

where:
$P(C_m|X)$ is the predicted accuracy (prior knowledge) of the m-th classifier given the feature X;
$P(\tilde{\theta}|X, C_m)$ is the probability of having $\tilde{\theta}$ for the given classifier;
$P(\theta|\tilde{\theta}, X, C_m)$ models the confusability (error pattern) of the classifier;
M is the total number of classifiers.

Once the output signals from the classifiers are combined, the final cognitive load level ($\theta^*$) is determined by $$\theta^* = \underset{\theta}{\operatorname{argmax}} P(\theta \mid X)$$

The method may involve a calibration phase where a user is given a set of standard tasks to perform that vary in complexity, such as starting with simple tasks and gradually becoming more difficult. The output measure from each task may be considered and, depending on the proximity of this measure to an optimized pre-set cognitive load target level for that task and user context, the next task is verified for appropriateness or changed.

The method may then involve a measurement phase where the user is asked to perform a task and the resulting output produced by the system is compared to the calibrated results to produce a measure of cognitive load.

The weightings used in the measurement phase may be user specific, based on the outcome of the calibration phase. Patterns that are more pronounced in reflecting the actual cognitive loads may be given a higher weighting.

Machine learning may be applied to weight features more heavily for particular users, say, if they give a better indication of the user's cognitive load fluctuations.

Dynamic learning may be applied to improve the individual classifications for new users.

Parameters of the individual classifiers and the fusion can be adjusted, for example through Bayesian Predictive Learning, to better reflect the characteristics of the new modality data acquired from users.

The input data stream specific to a particular task may correspond to a deliberate input by the person to the multimodal interface in the course of performing the task.

In another aspect the invention is a multimodal computer to measure a person's cognitive load while performing a task, comprising a user interface having one or more unimodal input and output devices, and a cognitive load analyser comprising:
 a receiver to receive one or more input data signal streams from the one or more unimodal input devices; and
 a classifier to identify predetermined "meta-interaction patterns" from the streams, and to weight the identified predetermined "meta-interaction patterns" to produce respective weighted outputs; and,
 a combiner to fuse the outputs to produce a measure indicating the person's cognitive load.

The interface may adapt its behavior to implement strategies that reduce cognitive load from use of the interface, and therefore increase task performance. Some options for behavioral adaptation include changes to:
 The materials used in the interaction;
 The volume of information flow;
 The format of communication; and
 The range of tasks presented to the user during periods of both high and low cognitive load.

One or more of the following input devices may be used by the interface:
 Video cameras to collect data about the user's appearance, expression, position, movement and speed.
 Infrared cameras to record the temperature of the user or user pattern detection.
 Eye gaze trackers to track the user's glances, including looking at input devices, dwell times and glancing away. These things might be indicative of attentiveness or disruptions.
 Accelerometers to detect the user's movement when it is too slight to be detected by the camera. Several accelerometers may be placed on the user's seat, on the floor, in the mouse or another handheld device where it is not noticeable for the user.
 Input device trackers and piezoelectric transducers to track the movements and pressure applied on each input device.
 Sound capture transducers such as microphones and microphone arrays to capture speech and other sounds, such as foot tapping, produced by the user, as well as ambient noise, self talk, and other involuntary voice sounds.
 Ultrasound to detect different kinds of spatial positioning of the user limbs and devices.

The input devices used by the interface may be those input devices deliberately used by the person in performing the task.

The interface may also involve a set of feature extractors to extract predetermined features, for example time or frequency domain analysis, from the incoming data streams. In this case the classifiers identify predetermined "meta-interaction patterns" from the features.

The classifiers may identify the patterns using one of more of the following models:

Gaussian mixture models.
Hidden Markov models.
Linear discriminant analysis.
Decision trees.
Artificial neural networks.
Other statistical or non-statistical models.

The classifiers may not be of the same model type, and a combination of model types within each feature stream and among different classifiers can be beneficial.

Input data signals streams received by the receiver, the "meta-interaction patterns" and weights of the classifier and fusion of the combiner may be specific to the person and/or task.

In a further aspect the invention is software operable when installed on a computer to interface with a user to measure the user's cognitive load.

BRIEF DESCRIPTION OF THE DRAWINGS

An example of the invention will now be described with reference to the accompanying drawings, in which.

BEST MODES OF THE INVENTION

The method of measuring the cognitive load typically takes place at a multimodal user interface of a computer. A task may be performed at the interface, or alternatively, the interface may assist in human-human interaction.

Figure 1:
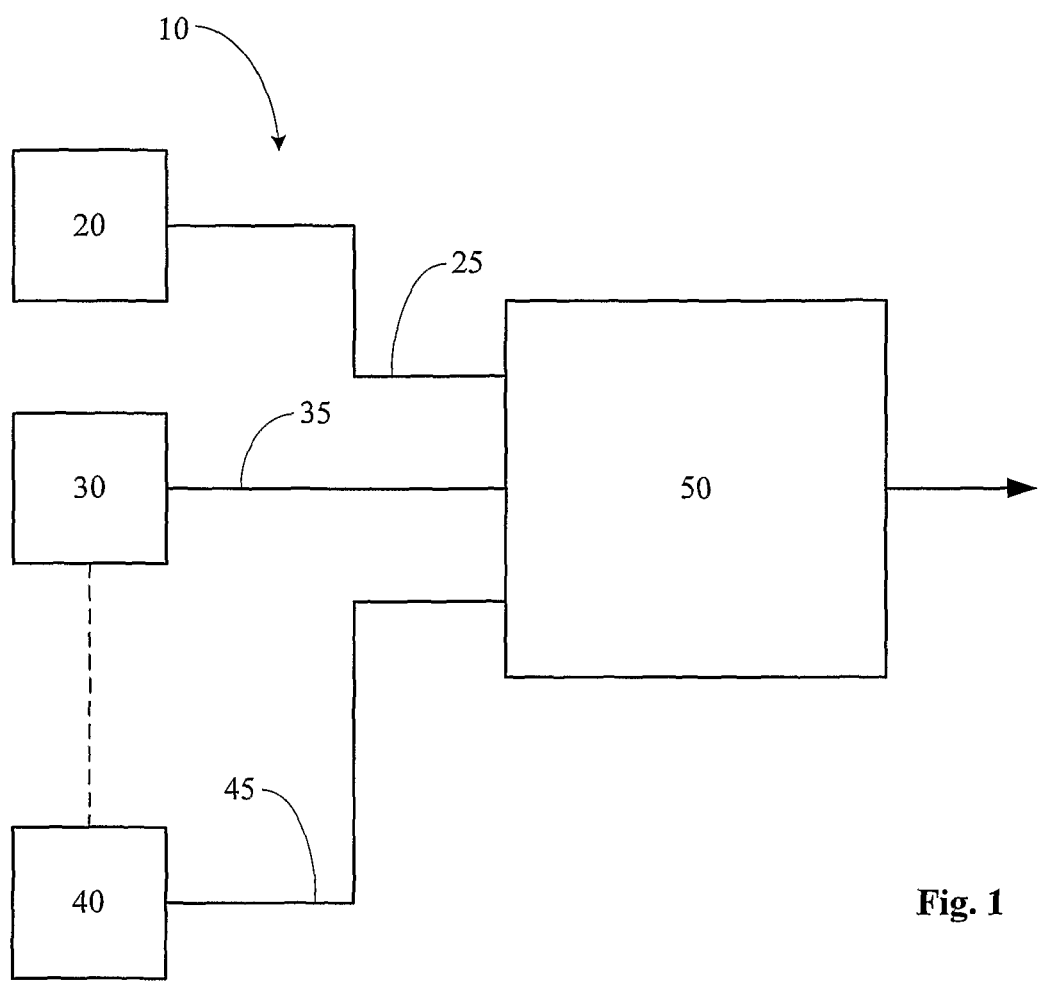
FIG. 1 is a block diagram of a multimodal interface of a computer.

Referring now to FIG. 1, the multimodal interface of a computer 10 offers a plural number of input and output modalities. The input modalities include a camera 20 to produce visual data, a microphone 30 to produce audio data and conventional input devices such as keyboard and mouse 40 to produce data. Other, more exotic, input modalities may be involved, such as speech recognition, eye-movement and gesture recognition.

A more complete list of the modalities that can be used for measuring the cognitive load of a user is:

Visual, including eye movements, facial expressions, head, body and hand gestures, as well as infrared red images of the head, body or hands.
Speech, including pitch and fundamental frequency and its associated higher order statistics, sound emissions (self-talk, mumbling) and speech rate.
Interaction events such as mouse hovering over selections, toggling between selections and typing and input method speed.
Task characteristics such as task complexity or difficulty, current stage or state of the task and completion rate.
User characteristics such as gender, age and education.
Physiological data such as heart rate and perspiration.

A more complete list of the sensor technologies that can be used to record the modalities is:

Video cameras to collect data about the user's appearance, expression, position, movement and speed.
Infrared cameras to record the temperature of the user or user pattern detection.
Eye gaze trackers to track the user's glances, including looking at input devices, dwell times and glancing away. These things might be indicative of attentiveness or disruptions.
Accelerometers to detect the user's movement when it is too slight to be detected by the camera. Several accelerometers may be placed on the user's seat, on the floor, in the mouse or another handheld device where it is not noticeable for the user.
Input device trackers and piezoelectric transducers to track the movements and pressure applied on each input device.
Sound capture transducers such as microphones and microphone arrays to capture speech and other sounds, such as foot tapping, produced by the user, as well as ambient noise, self talk, and other involuntary voice sounds.
Ultrasound to detect different kinds of spatial positioning of the user limbs and devices.

All sensors should be as inconspicuous as possible, so that they do not interfere with the user's interaction with the system. Each sensor will feed the captured data as a data stream, in this example three data streams are produced: a visual data stream 25, an audio data stream 35 and an input device data stream 45.

Figure 2:
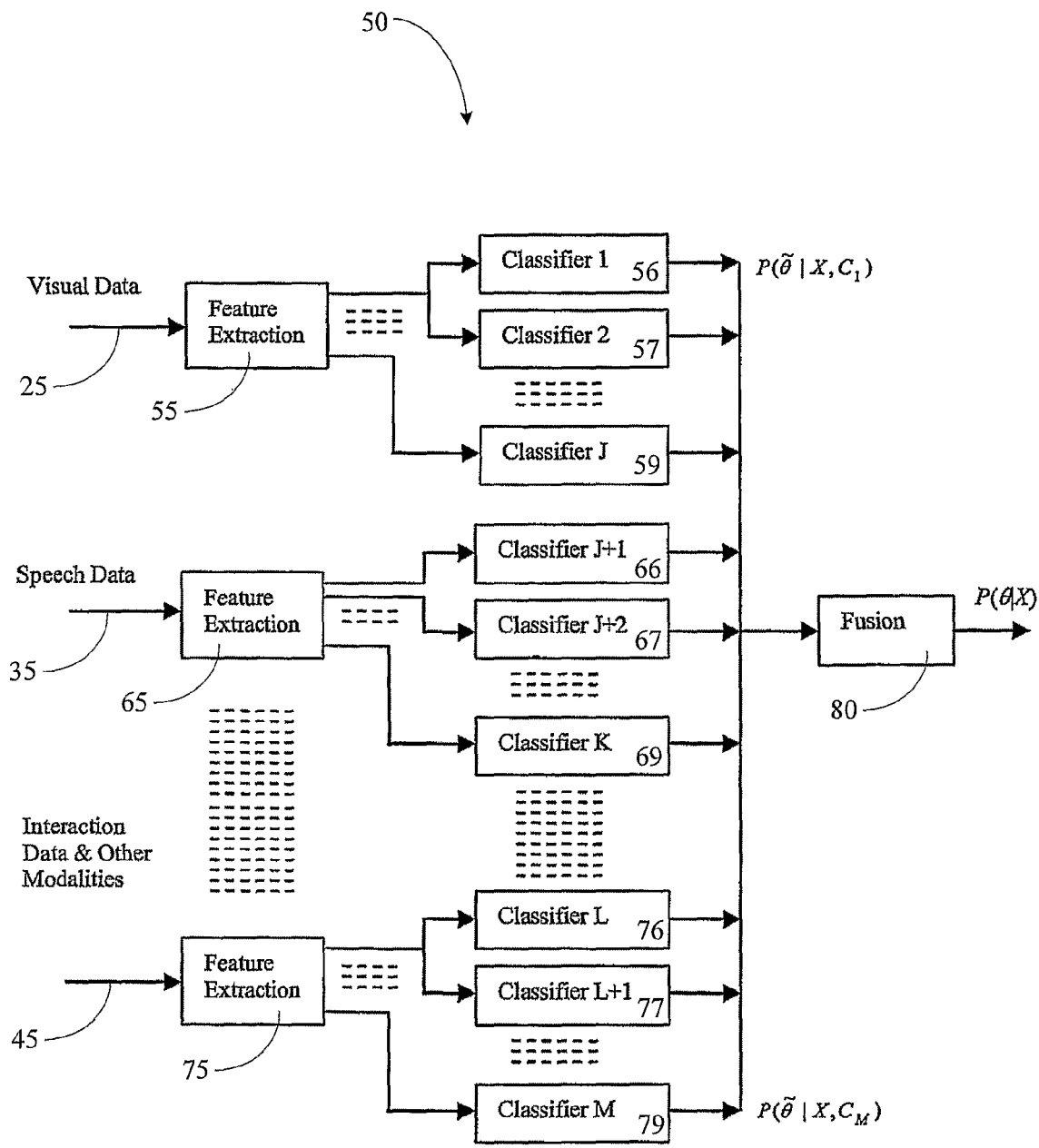
FIG. 2 is a block diagram of a cognitive load analyzer.

The computer 10 also comprises a cognitive load analyzer 50 which receives the data streams 25, 35 and 45, and this is shown in more detail in FIG. 2. The cognitive load analyzer may be the processor of the computer 10 that is programmed using software to operate in the manner described below.

The cognitive load analyzer 50 operates to receive input data streams 25, 35 and 45 at dedicated pre-processors (not shown) that operate to clean up the signals from the sensors 20, 30 and 40.

The clean signals are then passed to feature extraction modules 55, 65 and 75 that operate to identify epochs of interest and extract pre-determined signal features from the epochs of interest.

Downstream of each feature extraction module, there are a number of classifiers; so downstream of the visual feature extraction module 55 there are classifiers 56, 57-59, and so on. These classifiers operate to identify predetermined patterns of features from each stream. For instance, co-occurring features in different incoming signal streams can be 'bound' together to form a pattern.

Various models can be used to build the classifiers. Some of the more feasible ones include Gaussian mixture models, hidden Markov models, linear discriminant analysis, decision trees, and artificial neural networks. In addition, the classifiers need not be of the same model type and a combination of model types within each feature stream and among different classifiers can be beneficial.

The classifier detects predetermined patterns for the task that the user is performing. That is, the patterns may be different for different tasks. The patterns are then each given a user specific weighting and the classifiers produce an output signal related to the features they receive. Patterns that are more pronounced in reflecting the actual cognitive loads of the user are given a higher weighting. Once the features are weighted for that user, the output signals from the classifiers are combined together in fusion module 80 to acquire a measure of that user's cognitive load.

The fusion mechanism is based on a probabilistic framework that combines the outputs signals from various classifiers together, that is the probability of a set of features (X) indicating certain cognitive load level (θ) and is given by:

$$P(\theta \mid X) = \sum_{m=1}^{M} P(C_m \mid X) \sum_{\tilde{\theta}} P(\tilde{\theta} \mid X, C_m) P(\theta \mid \tilde{\theta}, X, C_m)$$

where:
- $P(C_m \mid X)$ is the predicted accuracy (prior knowledge) of the m-th classifier given the feature X;
- $P(\tilde{\theta} \mid X, C_m)$ is the probability of having $\tilde{\theta}$ for the given classifier;
- $P(\theta \mid \tilde{\theta}, X, C_m)$ models the confusability (error pattern) of the classifier;
- M is the total number of classifiers.

Once the output signals from the classifiers are combined, the final cognitive load level ($\theta^*$) is determined by $$\theta^* = \underset{\theta}{\operatorname{argmax}} P(\theta \mid X)$$

In general there will be a calibration phase where a user is given a set of standard tasks to perform that vary in complexity, starting with simple tasks and gradually becoming more difficult. The output measure from each task is considered and, depending on the proximity of this measure to an optimized pre-set cognitive load target level for that task, the next task is verified for appropriateness or changed.

During a subsequent measurement phase the user is asked to perform a task and the resulting output produced by the system is compared to the calibrated results to produce a measure of cognitive load.

Although the invention has been described with reference to a particular example, it should be appreciated that many variations and modifications are possible. For instance, the selection of user modality characteristics could be changed to any number of permutations and combinations. The user modalities could be selected to suit the user and/or the task. Also, using Machine Learning or other techniques, certain features could be weighted more heavily for particular users, say, if they give a better indication of the user's cognitive load fluctuations.

In order to train the system uniformly, a set of control tasks representative of the full range of possible induced cognitive load is required. Constructing such a set is a difficult task given the number of variables, and each user's prior knowledge and contexts. The invention may address this issue by incorporating dynamic learning in the measurement mode to improve the individual classifications for new users. Parameters of the individual classifiers and the fusion can be adjusted, for example through Bayesian Predictive Learning, to better reflect the characteristics of the new modality data acquired from users.

In addition, the benefits can also be used for future new users: if certain new tasks for one user are found to be inducing distinguished modality characteristics from the existing classifiers, then these tasks can be incorporated into the baseline training process to enhance the coverage of the training data. The collection and exchange of such data can be processed by a software module, possibly interconnected to other such modules by a data connection.

A side effect of measuring the cognitive load experienced by the user during each task could also be an indication of the cognitive load induced by different presentation strategies.

The cognitive load measurement could be employed for uses other than context-aware user modelling, for example:

Applying cognitive load variables into online task assignment.

Changing the presentation of the proceeding tasks in favour of preferred user modalities.

Breaking down the proceeding tasks into smaller, ordered sub-tasks.

Holding off or queuing less important or external tasks in preference of more important tasks.

Subtly altering the environment such that distractions are minimized.

A further example of the invention will now be described with reference to FIG. 2. In this example there are two multimodal input streams, being visual data 25 and speech data 35. Speech data 35 is captured by a microphone and fed through a speech recognizer. Gesture 25 is captured through video. Both of these inputs are connected and provided to a computer for further processing by the classifier and combiner as described below. The classifier and combiner are part of the processor of the computer, that is the processor is programmed by software to perform the functions of the classifier and combiner.

The task given to the user is a map-based task where the user is required to identify a number of places of interest on a map. The user is able to use both speech and gesture commands in isolation or in combination. The recognizers are able to store and filter the signals for feature information of interest and are chronologically synchronised to allow comparison of signals across modality streams.

Next, feature extraction is performed by the processor of the computer. The captured signals 25 and 35 are then sent through to the feature extraction modules 55 and 65. The features in the gesture input that may be captured are:
- Degree of shakiness in the gesture while pointing
- The size of the 'circles' used in selection (when circling an item)
- The extent to which gesture is used in the entire interaction (e.g. in 35% of constructions)

The features in the speech input that may be captured are:
- Delta-pitch (change in pitch at adjacent time sample)
- The frame energy in the speech signal
- The number of false-starts in the spoken command
- The number of hesitations in the spoken command The features of combined multimodal use that may be captured are:
- The relative temporal overlap between speech and gesture input
- The quantitative temporal overlap between speech and gesture input Next, a series of classifiers are then able to identify pre-determined patterns in the signal and gauge how well this feature fits the pre-determined pattern. The data is passed from the feature extraction modules 55 and 65 to the classifiers 56 to 59 and 66 to 69 respectively.

The determined patterns that the classifiers are comparing the extracted features to are particular to the user and task and will have been extracted from a calibration phase or from a profile type that is appropriate for that user.

For example, when analyzing the shakiness of the user's gesture input, the classifier may be just a threshold, where the shakiness is over X pixels, it becomes a point of interest. The classifier will be able to identify and mark the times when such events exceed the threshold. In addition, some classifiers may be combined requirements for two or more signals; e.g. the classifier can look for patterns of exceeding the gesture shakiness threshold coinciding with a hesitation in the speech signal.

The extent to which these modal signals fit the patterns determines the weighting of that feature. These results will be weighted at several levels, for example at the lowest level, if the signal is much higher than the threshold, then it is given greater weighting. In addition, some signals will be weighted more strongly simply because they are more indicative of cognitive load fluctuations for that user. For example, for this user, when the shakiness exceeds the threshold more than 5 times in a minute, that is a strong indication of high cognitive load. For another user this may be 10 times. The weighting can also be related to channel validity, for example, a weak signal that may be corrupt will automatically be given a lower weighting despite its significance to the user. Combined classifiers will produce again higher weightings than single modality classifiers.

The output from the classifiers is then passed to the fusion module 80. The fusion mechanism is based on a probabilistic framework that combines the outputs signals from various classifiers together. These can be fused at various levels of processing, and may have several levels of incremental fusion, where small sets of features that are available are combined together first, before being combined with all available features. For example, all gestural based features will be fused together first, as well as all speech based features, then the output from these will be fused at a second level.

Some features may not be used at all, if they do not contribute to the measurement of load, and have not reflected a sufficient change in to indicate a fluctuation in load. The more modal features are used the higher the level of confidence the end result will have.

The end construct may also include an indication of the modalities/modal features which provided more evidence of load fluctuations and this may be considered in choosing the next task or adjusting the user's profile to apply a higher weighting to that modal feature.

It is an advantage of this embodiment that input data signals are received from modal channels that are deliberately employed by the person completing the task. In this way the input data directly relates to the completion of the task, rather than non deliberate incidental actions such as head nods or other indicators of social activity.

It is a further advantage that particular input data streams are chosen specifically for the person performing the task. Further, the patterns and weightings can also be user specific. In this way an input data stream can be fused by the combiner in combination with other input data streams and/or in combinations with other input data streams.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Industrial Application

Cognitive load measuring is important to many situations, especially high intensity work situation and long distance education.

The scenario of high intensity work situations is typified by the magnitude of information required by the operators to make decisions that affect parts or the total environment under their control. Some examples include airplane take-off and landing, fire service, rail service, transportation management operators, ambulance service and others.

The workers need to make assessments in a matter of seconds and react appropriately, guided by the organization's operational procedures. Incidents handled can be crisis situations where human life is in danger. In such a high intensity, stressful situation, the operators need to be able to interact seamlessly with the technology available to them. Instead of hindering their access to information, the system should make it as easily accessible as possible, optimising the throughput of the information bandwidth between the user and the system; while allowing the user to remain in control of the interaction. If the system were able to reconfigure the interface to manage the flow of information to the user, depending on the user's cognitive state and current situation, the workers would be able to handle their tasks more effectively. The real time assessment and management of the user's cognitive load as detected by the system would enable such technological environments to be designed.

The learning cognitive load is a measure of the mental processing demand involved in learning tasks. When this demand is too high or low, learning is ineffective. The development of a voice analysis-based learning difficulty diagnosis program, which measures learning cognitive load, would contribute immediately to the improvement of education for rural and dispersed learners, who participate in tele-teaching, audio-conferencing, videoconferencing or who call help services, such as a help desk. The outcomes of this project could supply the teacher, tutor or help desk operator clearer information about students' learning difficulties than currently available diagnostic methods. It could also be used to diagnose learning difficulties in conventional educational settings, and to assist in the development of instructional programs. Implementations of this invention could help provide both teachers and students immediate feedback about their learning effectiveness.

The invention claimed is:

1. A computer implemented method for measuring a person's cognitive load, comprising the steps of:
    receiving two or more input data streams from an interface being used by a person while performing a task;
    identifying predetermined "meta-interaction features" based on the task from the two or more input data streams;
    identifying predetermined "meta-interaction patterns" from the "meta-interaction features" from two or more selected input data streams, including at least a first "meta-interaction pattern" identified from a predetermined combination of co-occurring "meta-interaction features" from two or more selected input data streams to form the predetermined combination;
    weighting each of the identified predetermined "meta-interaction patterns" based on the task to produce respective outputs; and
    fusing the outputs to produce a measure indicating the person's cognitive load.

2. A method for measuring a person's cognitive load according to claim 1, wherein the received two or more input data streams involve one or more of the following types of information:
    visual data, including data that captures one or more of eye movements, facial expressions, head, body and hand gestures;
    speech data, including one or more of pitch and fundamental frequency and its associated higher order statistics, sound emissions, speech rate, and information throughput;
    interaction events including one or more of mouse hovering, mouse trajectory, menu and button selections and typing and input method speed;
    task characteristics including one or more of task complexity or difficulty, current stage or state of the task, error rate, completion rate, and latency to respond;

person characteristics including one or more of gender, age and education; and
physiological data including one or more of heart rate and perspiration.

3. The method for measuring a person's cognitive load according to claim 1, wherein the patterns are identified using one of more of the following models:
gaussian mixture models;
hidden Markov models;
linear discriminant analysis;
decision trees; and
artificial neural networks.

4. The method for measuring a person's cognitive load according to claim 1, wherein any one or more of the following steps are specific to one or more of the person and task:
a further step of selecting two or more input data streams, identifying predetermined "meta-interaction patterns,"
weighting the identified predetermined "meta-interaction patterns," and
fusing the outputs.

5. The method for measuring a person's cognitive load according to claim 4, wherein each selected input data stream specific to the task corresponds to a deliberate input by the person to the interface in performing the task.

6. The method for measuring a person's cognitive load according to claim 1, wherein the method further comprises a calibration phase where the person is given a set of standard tasks to perform that vary in complexity.

7. The method for measuring a person's cognitive load according to claim 6, wherein an output measure from each task of the calibration phase is considered and, depending on the proximity of this measure to an optimized pre-set cognitive load target level for that task and person context, the next task is verified for appropriateness or changed.

8. The method for measuring a person's cognitive load according to claim 7, wherein the method further comprises a measurement phase where the person is asked to perform the task and the outputs produced by the method are compared to output measures of the calibration phase to produce a measure of cognitive load.

9. The method for measuring a person's cognitive load according to claim 1, wherein the weightings used in a measurement phase is person and/or task specific.

10. The method for measuring a person's cognitive load according to claim 1, wherein patterns that are more pronounced in reflecting actual cognitive loads are given a heavier weighting.

11. The method for measuring a person's cognitive load according to claim 1, wherein machine learning is applied to weight features more heavily for particular persons if they give a better indication of the person's cognitive load fluctuations.

12. The method for measuring a person's cognitive load according to claim 1, wherein dynamic learning is applied to improve the individual patterns for new persons.

13. The method for measuring a person's cognitive load according to claim 1, wherein parameters of individual classifiers and the fusion can be adjusted, to better reflect the characteristics of the new modality data acquired from the user.

14. The method for measuring a person's cognitive load according to claim 1, wherein one or more input streams are collected from the user in an unobtrusive manner.

15. Software operable when installed on a computer that can interface with a person to perform the method of measuring the person's cognitive load according to claim 1.

16. The method for measuring a person's cognitive load according to claims 1, wherein the interface is a multimodal interface.

17. A computer to measure a person's cognitive load while performing a task comprising an interface having unimodal input and output devices, the computer configured to execute computer readable medium, wherein the computer readable medium stores software instructions for a cognitive load analyzer, the cognitive load analyzer comprising:
a receiver to receive two or more input data streams from the unimodal input devices;
a set of feature extractors to extract predetermined "meta-interaction features" from the two or more input data streams;
a classifier to identify predetermined "meta-interaction patterns" based on the task from "meta-interaction features," wherein "meta-interaction patterns" have "meta-interaction features" from two or more data input streams, including at least a first "meta-interaction pattern" identified from a predetermined combination of co-occurring "meta-interaction features" selected from two or more input data steams to form the predetermined combination and to weight the identified predetermined "meta-interaction patterns" based on the task to produce respective weighted outputs; and
a combiner to fuse the outputs to produce a measure indicating the person's cognitive load.

18. A computer to measure a person's cognitive load according to claim 17, wherein one or more of the following input devices is used by the interface:
video cameras;
infrared cameras;
eye gaze trackers;
accelerometers;
input device trackers and piezoelectric transducers;
sound capture transducers; and
ultrasound capture devices.

19. The computer to measure a person's cognitive load according to claim 17, wherein the classifier identifies the patterns using one of more of the following models:
Gaussian mixture models;
hidden Markov models;
linear discriminant analysis;
decision trees; and
artificial neural networks.

20. The computer to measure a person's cognitive load according to claim 19, wherein multiple classifiers are used to identify the patterns and the classifiers are not of the same model type such that a combination of model types for each data stream and among different classifiers is used.

21. The computer to measure a person's cognitive load according to claim 17, wherein the interface is able to adapt to implement strategies that reduce cognitive load from use of the interface.

22. The computer to measure a person's cognitive load according to claim 21, wherein the behavioral adaptation includes any one or more changes to:
the materials used in the interaction;
the volume of information flow;
the format of communication; and
the range of tasks presented to the person during periods of both high and low cognitive load.

23. The computer to measure a person's cognitive load according to claim 17, wherein any one or more of the:
input data streams, "meta-interaction patterns," weight of the classifier, and fusion of the combiner, are specific to one or more of the person and task.

24. The computer to measure a person's cognitive load according to claim 17, wherein the one or more input devices used by the interface are those deliberately used by the person in performing the task.

* * * * *